(12) United States Patent
Magnin et al.

(10) Patent No.: US 8,636,307 B2
(45) Date of Patent: Jan. 28, 2014

(54) INTAGLIO PRINTING INKS

(75) Inventors: Patrick Magnin, Maxilly-sur-Leman (FR); Pierre Degott, Crissier (CH); Stéphane Chabrier, Lausanne (CH)

(73) Assignee: Sicpa Holding SA, Prilly (CH)

( * ) Notice: Subject to any disclaimer, the term of this patent is extended or adjusted under 35 U.S.C. 154(b) by 498 days.

(21) Appl. No.: 12/669,837

(22) PCT Filed: Jul. 14, 2008

(86) PCT No.: PCT/EP2008/059184
§ 371 (c)(1),
(2), (4) Date: Jan. 20, 2010

(87) PCT Pub. No.: WO2009/013169
PCT Pub. Date: Jan. 29, 2009

(65) Prior Publication Data
US 2010/0181753 A1 Jul. 22, 2010

(30) Foreign Application Priority Data
Jul. 20, 2007 (WO) .................. PCT/IB2007/002049

(51) Int. Cl.
*B42D 15/00* (2006.01)
*G09C 3/00* (2006.01)

(52) U.S. Cl.
USPC ............... 283/90; 283/67; 283/70; 283/72; 283/74; 283/96

(58) Field of Classification Search
USPC .............. 283/67, 70, 72, 74, 0.94, 95, 96, 90
See application file for complete search history.

(56) References Cited

U.S. PATENT DOCUMENTS

2006/0243160 A1* 11/2006 Sugerman ..................... 106/31.6
2006/0279909 A1* 12/2006 Kee ............................... 361/528

(Continued)

FOREIGN PATENT DOCUMENTS

CN 1375528 10/2002
DE 2426849 1/1975

(Continued)

OTHER PUBLICATIONS

English translation of Chinese Office Action for Chinese Application No. 20080025263.0, issued Feb. 16, 2012, pp. 1-12.

(Continued)

Primary Examiner — Dana Ross
Assistant Examiner — Justin V Lewis
(74) Attorney, Agent, or Firm — Greenblum & Bernstein, P.L.C.

(57) ABSTRACT

The present invention relates to printing inks for the intaglio printing process, also referred to as engraved steel die printing process. In particular, oxidatively curing inks comprising a combination of fusible wax and a UV curing binder component are disclosed. These inks can be printed on a standard printing press, and, through a short UV irradiation after printing, allow to significantly reduce or eliminate the undesired set-off which can occur after printing and stacking the printed sheets. Using the inks of the present invention results in less set-off contaminated printed sheets, allowing for a higher pile-stacking of the printed good, for the use of increased engraving depths, of a more challenging intaglio design, and for the printing on less porous substrates, while enabling the printing on a standard printing press, and offering the possibility of using a lower printing plate temperature.

30 Claims, 6 Drawing Sheets

(56) References Cited

U.S. PATENT DOCUMENTS

| | | | |
|---|---|---|---|
| 2007/0179211 A1* | 8/2007 | Leonard et al. | 522/71 |
| 2008/0051547 A1* | 2/2008 | Wakabayashi et al. | 528/18 |
| 2008/0241492 A1* | 10/2008 | Demartin Maeder et al. | 428/211.1 |

FOREIGN PATENT DOCUMENTS

| | | |
|---|---|---|
| EP | 0340163 | 11/1989 |
| GB | 2422611 | 8/2006 |
| JP | 01-289876 | 11/1989 |
| JP | 2002-38065 | 2/2002 |
| JP | 2002/038065 | 2/2002 |
| JP | 2003-64288 | 3/2003 |
| JP | 2003/566116 | 6/2005 |
| WO | 94/13749 | 6/1994 |
| WO | 01/38445 | 5/2001 |
| WO | 03/066759 | 8/2003 |
| WO | 2005/097927 A1 | 10/2005 |

OTHER PUBLICATIONS

Japanese Office Action issued with respect to patent family member Japanese Patent App. No. 2010-516483, mailed Jan. 22, 2013, along with an English Language translation.

* cited by examiner

−UV−C    5,44

INTAGLIO PRINTING INKS

FIELD OF THE INVENTION

The present invention relates to printing inks for the intaglio printing process, also referred to as engraved steel die printing process. In particular, oxidatively curing inks comprising a combination of fusible wax and a UV curing binder component are disclosed. These inks can be printed on a standard printing press and allow to significantly reduce or eliminate the undesired set-off which can occur after printing and stacking the printed sheets. Using the inks of the present invention results in less set-off contaminated printed sheets, allowing for a higher pile-stacking of the printed good, for the use of increased engraving depths, of a more challenging intaglio design, and for the printing on less porous substrates, while enabling the printing on a standard printing press, and offering the possibility of using a lower printing plate temperature.

BACKGROUND OF THE INVENTION

In the engraved steel die printing process, hereafter called intaglio printing process, a rotating engraved steel cylinder, carrying a pattern or image to be printed, and heated to a temperature of the order of 80° C., is supplied with ink by one or more template inking cylinders. Subsequent to the inking, any excess of ink on the plain surface of the printing cylinder is wiped off by a rotating wiping cylinder. The remaining ink in the engraving of the printing cylinder is transferred under pressure onto the substrate to be printed, which may be a paper or plastic material in sheet form, while the wiping cylinder is cleaned by a wiping solution. Other wiping techniques can also be used, such as paper wiping or tissue wiping ("calico").

One of the distinguishing features of the intaglio printing process is that the film thickness of the ink transferred to the substrate can be varied from a few micrometers to several tens of micrometers by a correspondingly shaped printing plate. This ability to vary the film thickness is a most desirable feature of the intaglio printing process and can be used to produce embossing effects, i.e. to confer tactility to the printed document, as well as to produce shade variations using one and the same ink.

The pronounced relief of the intaglio printing accentuates the problem of "set-off", which is the transfer of ink from one printed sheet to the back side of the next following printed sheet in a stack, or to the back of the endless sheet in a web. The factors influencing the "set-off" are determined by the printing ink formulation, the engraving depth and evenness, the printing conditions, the printing substrate, the number of stacked sheets per pile, the time between printing and handling of the piles and the way how the printed piles of paper are handled after printing.

The "set-off" caused by the residual tackiness of the printed ink, which adheres to the substrate surface of the back of the next sheet, is aggravated when pressure is applied to a pile of stacked printed sheets. Depending on its extent, "set-off" can irreversibly spoil the printed product affected by it. A classical method to avoid losses of printed good due to "set-off" is to interleave separation sheets between all printed sheets; this leads however to a slowing down of the printing process and also to a more expensive printing.

The problem of reducing set-off in oxidatively curing inks has been addressed in the art in several ways:

by using high molecular weight oxidatively curable binders, by solvents with relatively low boiling point which would partially evaporate on the printing plate, by waxes, forming a protective layer on the ink film, by a high filler to binder ratio which would reduce the residual tackiness of the ink, and by efficient metal catalysts which ensure the rapid through-curing of the printed ink film.

WO 03/066759 (and the related JP 2002-38065 and JP 01-289876) disclose a dual-curing ink matrix, comprising a UV curable material as the principal component (around 40 wt-%), together with an oxidatively curing alkyd resin as a secondary component (around 5 wt-%), a photoinitiator, and an oxidative polymerization catalyst. The disclosed ink composition does not comprise fusible wax.

This ink is subjected to UV curing immediately following the printing operation, whereupon it instantly dries, at least at the surface, with the consequence that set-off cannot occur. A slower, in-depth post-curing takes place during the following hours and days according to an oxypolymerization mechanism, allowing for a good adhesion of the ink to the substrate even in the presence of UV-opaque pigments or fillers.

The ink according to WO 03/066759 requires particular, e.g. EPDM rubber equipped, printing presses, designed for the printing of UV curing inks; the ink cannot be printed on an Intaglio printing press equipped for printing standard oxypolymerization curing, greasy inks.

WO 01/38445 A1 addressed the "set-off" of intaglio printing inks on polymer substrates. The binder of the therein disclosed intaglio printing ink includes an auto-oxidizable polyester resin having fatty acid residues, and a wax dispersion having a glass transition temperature below the maximum temperature achieved during the printing process. The disclosed printing ink further includes solvents and pigments and can be cured under UV radiation. This printing ink contains no acrylates at all.

The majority of intaglio printing inks used today are still alkyd based, greasy inks, which cure according to a purely oxidative drying mechanism. They traditionally contain hydrocarbon solvents. In consequence, the printing machines in the majority of printing works are equipped with inking systems, printing blankets and wiping cylinders which are specifically designed to resist to the alkyd- and hydrocarbon solvent-based chemistry of these traditional intaglio printing inks, but which, in turn, do not resist to the more polar UV-ink chemistry.

Oxidatively drying alkyds, as compared to UV-curing inks have, however the shortcomings of an inherently slow drying, which results in a lower production rate, of the need to use environment-unfriendly organic solvents (VOC=volatile organic compounds), and of the intrinsic proneness of these inks to produce "set-off" as a consequence of their slow drying. Their main advantage, in turn, is a good in-depth curing provided by the oxidative drying mechanism, resulting in good physical and chemical resistances of the printed and dried product. The printing equipment adapted to print them is furthermore already in place at every printing work.

UV-curing intaglio printing inks, on the other hand, have the advantage of a fast or almost immediate surface drying, eliminating waiting times and allowing for a high production rate. The presence, in the ink formulation, of volatile organic compounds can be avoided, and set-off does not occur due to the instant-drying.

The shortcomings of UV-inks, in turn, are that in-depth curing remains a challenge, in particular in case of a high pigment loading in the ink and/or the presence of pigments which are opaque or which have a high absorbance in the UV spectrum. UV-curable intaglio printing inks are furthermore significantly more expensive than traditional alkyd based inks, and, even more important, the printing equipment needs a major change of all components which come into contact with the UV-curable printing ink, in particular the rollers made of rubber or other polymer materials, which must be redesigned to resist the different chemistry of the UV-inks.

The chemical composition of UV-curing intaglio printing inks is noteworthy entirely different from that of alkyd-/hydrocarbon solvent based intaglio printing inks. When UV-curable intaglio printing inks come in contact with the alkyd-/hydrocarbon solvent-specific rubber components of the inking system, the printing blankets and the wiping cylinders of the printing machine, they can cause a swelling or shrinking of the rubber, which in turn alters the geometry of the rollers and blankets. This results in a low printing quality, as well as in a reduced roller lifetime, altogether increasing the printing and maintenance cost.

In practice, to allow for the printing of UV-curing intaglio inks, the rollers of the printing machine must be made of a special material or protected by a highly resistant compound such as non-polar EPDM rubber (ethylene propylene diene monomer rubber). Thus an additional cost arises for the printer if he changes from traditional alkyd-based intaglio inks to energy-curable intaglio inks, which is caused on the one hand by the more expensive energy-curable (UV-curable) intaglio printing ink itself, and on the other hand by the expensive upgrade of the printing equipment to become UV-ink compliant. A further disadvantage results for the printer who needs to print in both technologies, because each time he changes the type of printing ink (UV-curable or oxidatively curable, respectively), all corresponding parts of the printing machine must be changed accordingly in a time-consuming operation.

It would thus be highly desirable to have available an ink which combines the favorable set-off properties of the UV intaglio inks with the good in-depth curing of the alkyd intaglio inks, which results in high physical and chemical resistances of the printed ink on the document, and which is compatible with (i.e. printable without change on) the existing intaglio printing equipment in place at the printers' premises.

It is the object of the present invention to provide an intaglio printing ink which has very good set-off resistance and in-depth curing values, and which can be printed on the conventional intaglio printing equipment designed for oxidatively curing inks.

SUMMARY OF THE INVENTION

The present invention is related to an intaglio printing ink composition comprising as a principal component an oxidatively curable material, such as an alkyd resin or a modified alkyd resin, and, as an auxiliary component, a combination of a UV curable material and of a fusible wax, characterized in that said composition, after a thermal cycling from 25° C. to 80° C., to 25° C., and after irradiation with a curing dose of UV light, shows an increase in its complex dynamic modulus of at least 50%, preferably at least 100%.

The thermal cycling used in the present invention corresponds to the ink's typical variation of temperature during the conventional intaglio printing process. The temperature of the intaglio plate during the printing operation is traditionally chosen to be around 80° C., and the inks are formulated in consequence as to the melting temperature range of their fusible wax components. The inks of the present invention, having a particular mechanism to increase viscosity after printing, allow for more freedom in choosing the printing plate temperature. In particular, inks containing temperature-sensitive components can be formulated so as to be printable at a lower temperature, such as 60° C. or even 50° C., whilst still obtaining a good set-off resistance of the freshly printed sheets.

According to the present invention, a curing dose of UV light means a dose which would dry-cure a corresponding UV-ink.

Said increase in complex dynamic modulus means that the printed ink is gelling following the UV-irradiation, and in consequence loses much of its initial tackiness. The dynamic modulus is a measure for the ink's rheologic behavior; an increase of this modulus by 50% is highly significant with respect to set-off resistance.

In particular, the ink according to the present invention has, as a principal component, an oxidative curing material in an amount between 20 and 50 wt-% of the total printing ink, which provides it with good in-depth drying properties, and, as an auxiliary component, a combination of fusible wax in amounts up to 10 wt.-%, preferably between 2 and 5 wt-%, and a UV curing material in amounts between 2 and 15 wt-%.

It was found that the said combination of fusible wax and the UV curing component allowed the printed ink to be surface-stabilized through a short UV irradiation following the printing operation, so as to avoid set-off, while still being printable on standard printing equipment at full printing speed, but allowing for a higher stacking of the printed goods. The good in-depth curing and the physical and chemical resistances of traditional oxidatively curing intaglio inks are maintained.

The ink of the invention has chemical properties which are close to the ones of traditional intaglio inks, and it can, for this reason, be printed on a conventional intaglio printing press, without the need for changing the rubber parts on the printing machine which come into contact with the printing ink. The only requirement for the printer is the additional presence of a UV irradiating unit on an otherwise standard intaglio printing press.

The intaglio printing ink of the present invention is principally an oxidatively curing intaglio ink, which in addition to wax, comprises a UV-curable component, preferably in an amount of 2 to 15 wt-%, more preferably of 4 to 8% by weight of the total printing ink composition. Through a UV exposure immediately after the printing operation, the printed ink surface is stabilized, so as to allow a stockpiling (stacking) of the printed sheets, without producing "set-off" even under particularly unfavorable conditions. Significantly higher stacks of printed goods can therefore be envisaged.

The ink of the present invention is, however, not dry after the short UV irradiation following the printing operation. This is evidenced by the fact that, under strong pressure, the printed and UV-irradiated ink of the present invention nevertheless transfers to a second sheet of substrate, whereas a printed and UV-irradiated UV-curing ink does not. The surface and in-depth curing of the ink of the present invention takes place during the hours or days which follow the printing operation, through an oxypolymerization process under the influence of air oxygen, as known for traditional intaglio inks.

The formulation of oxidatively curing inks is known to the skilled person. Such inks comprise an oxidatively curable material and an oxypolymerization catalyst (drier). Oxidatively curable materials, useful as the oxidatively curable component, can be of natural or synthetic origin. Typical oxidatively curing materials of natural origin are oligomers or polymers based on vegetable oils, such as linseed oil, tung oil, tall oil, as well as other drying oils known to skilled person. Typical oxidatively curing materials of synthetic origin are alkyd resins, such as can be obtained, as known to the skilled in the art, for example by the joint condensation (esterification) at 180° C. to 240° C. of one or more polycarboxylic acids, such as ortho-, iso-, or ter-phthalic acids, ortho-tetrahydrophthalic acid, fumaric acid, maleic acid, or a corresponding anhydride thereof;

one or more polyhydric alcohols, such as glycol, trimethylolethane, pentaerythritol, sorbitol, etc.; and one or more unsaturated fatty acids, such as linseed oil, tung oil or tall oil fatty acids.

Such oxidatively curable components are present in the ink according to the invention preferably in amounts of 20 to 50% by weight, most preferably of 30 to 45% by weight, of the total printing ink.

The UV-curable material, useful as the UV-curable component, can be selected from the group of acrylate monomers, oligomers or polymers, such as amino acrylates, epoxy acrylates, polyester acrylates, urethane acrylates, self-photoinitiating oligomer acrylates, dendritic acrylates, as well as mixtures thereof. Preferred UV-curable components are acrylate oligomers and polymers.

The intaglio printing ink of the present invention further comprises at least one siccativating agent, i.e. an oxypolymerization catalyst, which may be the salt of a long-chain fatty acid with a polyvalent metal cation, such as cobalt(2+), vanadyl(2+), manganese(2+), or cerium(3+). Salts of the said type are oil soluble and thus compatible with fatty alkyd based inks. The ink may further comprise soaps of calcium and/or zirconium and/or cerium as a co-siccativating agent to further improve the in-depth curing. The siccativating agent is usually present in amounts of up to 5% by weight, preferably of 1 to 3% by weight, of the total printing ink composition.

The intaglio printing ink of the present invention further comprises at least one photoinitiator for initiating the polymerization reaction of the UV-curable components. The photoinitiator is usually present in amounts of up to 5% by weight, preferably of 1 to 3% by weight, of the total printing ink composition. Suitable photoinitiators are known to the skilled person and are e.g. of the acetophenone type, the benzophenone type, the α-aminoketone type, or, preferably, the phosphine oxide type. One suitable photoinitiator is Irgacure 819 from Ciba.

The intaglio printing ink composition may further comprise photoinitiator stabilizers (UV stabilizer) in an amount of up to 3%, preferably of 0.5 to 3%, more preferably of 1.5% by weight of the total printing ink.

The inventors further found out that the simultaneous presence of, on the one hand, fusible wax, which is known to reduce the "set-off" in traditional intaglio printing inks, and, on the other hand, UV-curable acrylates, resulted in a synergistic effect in preventing the "set-off" of the printed intaglio inks of the present invention to a dramatic and unexpected degree, if the inks are subjected to UV irradiation immediately after the printing operation.

The intaglio printing ink of the present invention thus further comprises at least one fusible wax, such as a Montan wax based material, e.g. refined Monatan wax, Montanic-acid, -amides, or -esters; modified or saponified Montan wax, or Carnauba wax, or other similar synthetic long chain ester wax or mixtures thereof. The fusible wax or waxes are comprised in the intaglio printing ink of the present invention in amounts of up to 10% by weight, preferably between 1 to 10%, more preferably between 1 to 5%, and even more preferably between 2 to 5% by weight of the total printing ink.

Within the context of the present invention, fusible wax refers to a wax or a wax mixture having a melting point or a melting interval of the neat product in the range of between 50-120° C., preferably of between 55-100° C., more preferably of between 60-85° C. In the printing ink composition, the corresponding melting points or melting intervals of the wax are lowered due to the presence of other compounds.

The intaglio printing ink composition may further comprise other components such as pigments for providing the color of the ink, fillers, emulsifiers, solvents, e.g. for the viscosity adjustment, as well as special additives and/or markers for security or forensic purposes.

DETAILED DESCRIPTION OF THE INVENTION

The intaglio printing ink composition of the present invention comprises at least one oxidatively curable principal component, preferably in amounts between 20 and 50 wt-% of the total ink composition, at least one UV-curable component, preferably in amounts between 2 and 15 wt-% of the total ink composition, at least one oxypolymerization drier, at least one photoinitiator, and at least one fusible wax, preferably in amounts between 1 to 10 wt-%, of the total ink composition. Optionally, pigments, fillers, additives and solvents, as well as a stabilizing agent for the UV-curing part, may be present.

The oxidatively curable component can be selected from the group consisting of the alkyd resins and the modified alkyd resins of synthetic or natural origin, in particular phenol-, epoxy-, urethane-, silicone-, acryl- and vinyl-modified alkyd resins, neutralized acid alkyds, and siccativating vegetable oils. Typical oxidatively curing materials of synthetic origin are the alkyd resins obtained by esterification of a mixture of one or more polyhydric carboxylic acids or acid derivatives, such as anhydrides and/or their hydrogenated equivalents, and one or more unsaturated fatty acids of natural origin, with one or more polyols, such as ethylene glycol, glycerol, pentaerythritol etc. Examples for such alkyd resins are disclosed in EP 0 340 163 B1, the respective content thereof being incorporated herein by reference, in particular the examples II and III.

The oxidatively curable component is present in amounts of 20 to 50% by weight, preferably of 25 to 40% by weight, and most preferably in an amount of 30 to 35% by weight of the total printing ink.

The siccativating agent (drier), i.e. the oxypolymerization catalyst, is added to promote the in-depth curing of the alkyd under the influence of air oxygen. Said drier is typically based on transition metal salts which are soluble in the oil based printing ink medium. The ions of the chemical elements with numbers 23 to 29, as well as those of certain other chemical elements, are potentially useful in driers. Particularly preferred is a combination of cobalt and manganese carboxylates, or of cobalt, manganese and zirconium carboxylates, wherein the carboxylate is a long-chain carboxylic acid anion. A particularly preferred drier comprises cobalt(II) octoate, manganese(II) octoate, and zircon(IV) octoate in a hydrocarbon solvent. Other suitable driers have been disclosed in co-pending patent application EP07112020.8 of the same applicant. The drier is present in amounts of up to 5%, preferably 0.5 to 5 wt-%, and more preferably of 1 to 3 wt-% of the total printing ink.

The UV-curable component is preferably an acrylate, a monomer or preferably an oligomer or polymer. Said acrylate may be selected from the group consisting of the amino acrylates, the epoxy acrylates, the polyester acrylates, the urethane acrylates, the self-photoinitiating oligomeric acrylates, the dendrimeric acrylates, and mixtures thereof. Examples of suitable UV-components are given in Table 1.

TABLE 1

| Resin Type | Trade Name | Supplier |
|---|---|---|
| acrylate monomers | TMPTA, HDDA, NPGDA, PETA, and many other products from different suppliers | Cytec and many other suppliers |
| amino acrylates | Genomer 5275 | Rahn |
|  | Uvecryl P115 | UCB |
| epoxy acrylates | Craynor 132 | Sartomer |
|  | Laromer LR 8765 | BASF |
| polyesters acrylates | Ebecryl 450 | Cytec |
| urethanes acrylates | Photomer 6618 | Cognis |
|  | Actilane 245 | Akzo |
|  | Ebecryl 2003 | Cytec |
|  | Ebecryl 220 | Cytec |
| dendritic acrylates | BDE-1029 | IGM Resins |
|  | BDE 1025 | IGM Resins |
| Self-photoinitiating oligomer acrylate | Drewrad 1122 | Ashland |
| Acrylate oligomer | Ebecryl 600 | Cytec |

The UV-curable component is preferably present in an amount of 2 to 15% by weight, more preferably of 4 to 8% by weight, most preferably of 5 to 7% by weight, of the total printing ink.

The intaglio printing ink of the present invention further comprises at least one photoinitiator. Said photoinitiator is typically present in amounts of up to 5% by weight, preferably of 0.5 to 5% by weight, more preferably in amounts of 1 to 3% by weight, and most preferably of 1 to 2% by weight of the total printing ink.

Suitable photoinitiators can be chosen from the group consisting of the α-aminoketones (e.g. Irgacure 369, Irgacure 907), the α-hydroxyketones (e.g. Irgacure 2959), the phosphine oxides (e.g. Irgacure 819), the thioxanthones (e.g. ITX), the oligomeric thioxanthones (e.g. Genopol TX-1), the oligomeric amino benzoates (Genopol AB-1), the oligomeric benzophenones (e.g. Genopol BP-1). These types of photoinitiators are known to the skilled person; they generate free radicals upon UV irradiation, initiating a radical polymerization reaction of the UV curable component, such as the acrylate.

Fusible waxes suitable to carry out the present invention may be chosen from the group of refined Montan wax, Montanic-acid, -amide, -ester; modified or saponified Montan wax, Carnauba wax, long chain ester wax, and mixtures of these. Examples of suitable waxes are given in Table 2. The melting point or melting range of the fusible wax suitable to carry out the invention is between 50 to 120° C., preferably between 55 to 100° C., more preferably between 60 to 85° C.

TABLE 2

| Type of Wax | Trade Name | Melting Point* |
|---|---|---|
| Refined Montan wax | Licowax U | ~86° C. |
| Montanic acids | Licowax S | ~82° C. |
|  | Licowax SW | ~83° C. |
|  | Licowax LP | ~83° C. |
|  | Licowax UL | ~83° C. |
|  | Licowax NC | ~84° C. |
| Esterified Montanic acids | Licowax E | ~82° C. |
|  | Licowax F | ~79° C. |
|  | Licowax KP | ~87° C. |
|  | Licowax KPS | ~82° C. |
| Esterified, partly saponified Montanic acids | Licowax O | ~100° C. |
|  | Licowax OP | ~100° C. |
|  | Licowax OM | ~89° C. |
| Montan based | Printwax MM8015 | ~95° C. |
| Montan/Carnauba | Printwax MX6815 | ~90° C. |

The indicated melting points are those given by the suppliers for the neat wax.

Licowax is supplied by CLARIANT

Printwax is supplied by DEUREX GmbH, Toglitz

Other type of waxes, such as paraffin, polypropylene, polyethylene amide or PFT waxes and the like, can be further comprised in the printing ink composition of the present invention without disturbing the synergistic effect on the set-off displayed by the simultaneous presence of fusible wax and acrylate under UV irradiation immediately after printing. They may be used for adjusting other properties of the intaglio printing ink, such as rub resistance or rheological behavior, as known to the skilled person.

According to a further aspect of the invention, a photoinitiator-stabilizer (UV-stabilizer) may also be comprised in the ink. Such photoinitiator-stabilizers are known to the skilled person. Useful stabilizers are e.g. Florstab UV-1, supplied by Kromachem, and Genorad 16, supplied by Rahn.

Said photoinitiator-stabilizer is comprised in the ink in an amount of up to 3%, preferably of 0.5 to 3%, more preferably in an amount of 1 to 2%, most preferably in an amount of 1.5% by weight of the total printing ink.

The presence of the UV-stabilizer serves to avoid a premature polymerization during the preparation or during the handling of the ink prior to use on the printing press as well as prior to the radiation-curing step. Furthermore, the UV-stabilizer provides a longer shelf live to the printing ink.

The intaglio ink of the present invention further may comprise pigments and fillers, as well as mineral solvents. The pigment content of intaglio printing ink composition is generally in the range of 3 to 30%, more usually in the range of 5 to 15%, by weight of the total printing ink. Suitable pigments for use in intaglio inks are known to the skilled person.

According to a further aspect of the invention, the filler content of the printing ink composition may be in the range of 5 to 50%, by weight of the total printing ink. The filler can be e.g. of natural origin, such as chalk, china clay, exfoliated mica, or talcum, or synthetically prepared, such as precipitated calcium carbonates, barium sulfate, bentonite, aerosil, titanium dioxide, or also mixtures of some of these.

Suitable mineral solvents for embodying the present inventions are linear or branched organic hydrocarbon solvents with chain lengths of $C_{10}$ to $C_{15}$ and having a boiling point between 180 and 290° C., such as PKW 1/3, PKW 4/7 AF, PKWF 6/9 neu or PKW 6/9 AF (e.g. from Halterman), as well as fatty acid esters. Oxygenated or polar solvents, such as glycol ethers, may be added as co-solvents.

The viscosity of the ink is adjusted with mineral solvent and additives, e.g. Aerosil, to about 1 to 40 Pa·s, preferably about 3 to 25 Pa·s, more preferably to about 6 to 15 Pa·s, measured on a cone-plate geometry at 1000 $s^{-1}$ and 40° C.

The intaglio printing ink of the present invention is preferably prepared according to the following process, comprising the steps of:

a) grinding together, preferably on a three-roll mill, at least one oxypolymerization-curable component, such as an alkyd resin, at least one UV-curable component, such as an acrylate, at least one fusible wax, and optional fillers and solvents, to obtain a homogeneous dispersion;

b) grinding together, preferably on three-roll mill, at least one oxypolymerization-curable component, such as an alkyd resin, at least one pigment, and optional fillers and solvents to obtain a homogeneous dispersion;

c) mixing and grinding together the dispersion of step a), the dispersion of step b), an oxidative drier (siccativating agent), a photoinitiator and an optional photoinitiator stabilizer, to obtain the printing ink of the invention.

A first oxypolymerization-curable component, such as an alkyd resin, may be used in step a) and a second, different oxypolymerization-curable component, such as an alkyd resin, in step b), in order to assure best compatibility with the UV-curable acrylate and with the pigment, respectively.

Care must be taken during the mixing together of the printing ink components that the temperature does not exceed 50° C., because the UV curable component, such as an acrylate component, may undergo a premature polymerization reaction, making the ink useless for further application. For this reason, the mixing of the ink components is preferably carried out on an open three roll mill system rather than in a ball mill mixing equipment.

As will be appreciated by the skilled person, the production of the ink according to the present invention is not restricted to the indicated process; however, using the indicated process prevents any uncontrolled heating of the printing ink and therefore offers some guarantees against the premature and uncontrolled polymerization of the acrylic components during the ink manufacturing step.

The inventors have found that there is an inherent correlation between the "set-off" shown by an intaglio printing ink and its internal structural properties, sometimes also referred to as the cohesion force or cohesive strength, which can be considered as the force which is necessary to disrupt an applied coating layer (film splitting).

The complex dynamic modulus G* is a measure for the said cohesive strength of the ink, and is defined as:

$$G^* = G' + iG''$$

wherein G' is the elastic modulus (also called storage modulus), and G" is the plastic or viscous modulus (also called loss modulus).

The inventors surprisingly found that the simultaneous presence of fusible wax and a moderate amount of UV-curable acrylate oligomer significantly increased G* after thermal cycling, followed by exposure of the ink to UV light. In other words, the internal cohesion of the ink increased, which turned out to strongly decrease the "set-off" tendency of the ink:

Due to the simultaneous presence of the fusible wax and the UV curable component, after irradiation of the printed intaglio ink of the present invention by UV light following the printing operation, involving a thermal cycling of the ink, no "set-off" was observed any more, as is the case for UV-irradiated UV-curing inks. In contrast to UV-curing inks, the ink of the present invention is, however, not "dry" after the UV-irradiation, and only dries through oxypolymerization during the following hours and days. The present ink remains, as to its principal parts, an oxidatively curing intaglio ink having good in-depth drying and long-term mechanical and chemical resistances, which can be printed using standard printing equipment with rubber parts designed for printing greasy alkyd inks, given that a UV-irradiation unit is present on the printing press.

The UV-radiation may hereby be generated by conventional mercury UV-lamps, electron-less bulb UV-lamps, pulsed UV-lamps, UV-light-emitting-diodes (UV-LED's) and the like, capable of emitting UV-A, UV-B, and/or UV-C radiation.

A method of intaglio printing, using an intaglio printing ink according to the present invention, comprises thus the steps of a) intaglio-printing the ink onto a substrate, hereby cycling the ink's temperature from room temperature to printing plate temperature and back to room temperature; b) subjecting the printed document to UV-radiation following the printing operation; and c) storing the printed document for several days, to allow for oxidative curing of the printed ink.

According to the present invention, room temperature is meant to be 25° C. The printing plate temperature is typically 80° C., as described above, but with specific inks can be as low as 50° C.

The features of the disclosed intaglio ink result in a neat advantage for the printer, who can run his standard intaglio press with higher efficiency and versatility. These improvements are reached through the synergistic effect onto the "set-off" tendency of the printed ink of small amounts of both, fusible wax and UV-curable acrylates.

The present invention will now be described in more detail with reference to non-limiting examples and drawings.

FIG. 1 shows a plot of the experimentally determined complex dynamic modulus (G*, Pa), measured before and after heat-cycling (25° C.-80° C.-25° C.) of the ink, against the experimentally determined set-off resistance value (determined according to the method given below on an empirical scale going from 1 (bad) to 6 (excellent)) for four different intaglio inks of the prior art, each without and with a fusible wax component.

FIG. 2a-c illustrate the synergistic effect of the simultaneous presence of fusible wax and UV-curable acrylate in an intaglio ink to prevent set-off after printing for the following example 1 and comparative examples 1 to 3. In detail:

Figure 1:
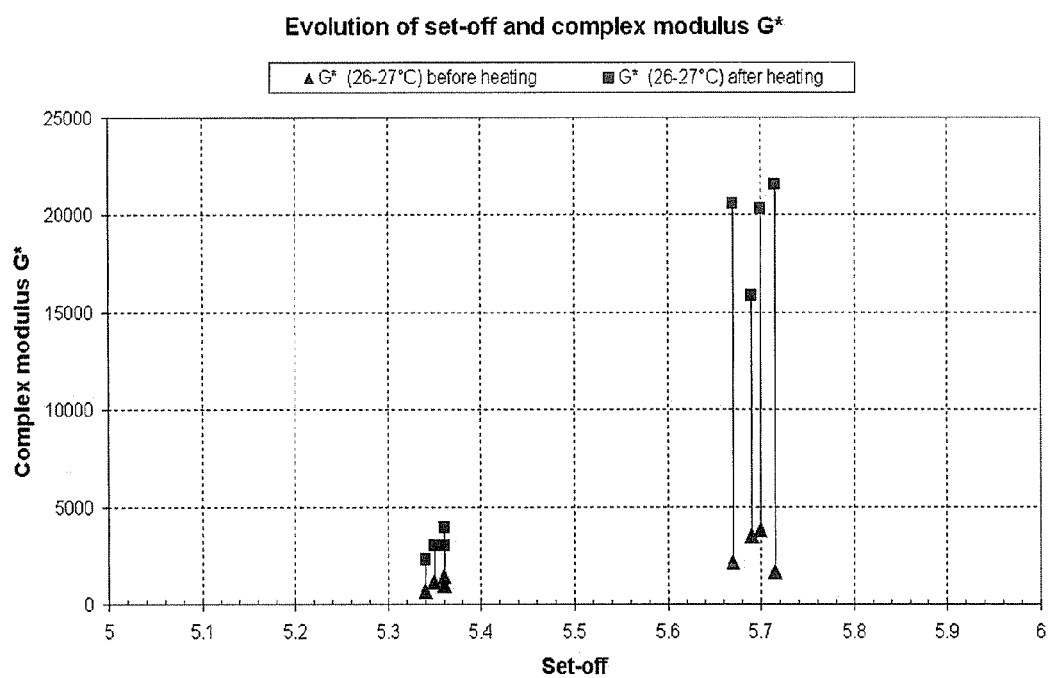

FIG. 4a-d illustrate the cooperative effect of a UV-curable component and a fusible wax onto the set-off properties of the inks, as exemplified with example 1 and comparative example 1.

EXAMPLE 1

Ink of the Present Invention ("Modified 30")

An intaglio ink according to the present invention was prepared as follows (the amounts are given as wt.-% with respect to the final ink composition):

A first part of the ink was prepared by combining the following components, and grinding them on a conventional three-roll mill (Bühler SDY-200), as known to the skilled in the art, so as to form a homogenous dispersion:

| Part I | |
|---|---|
| Component | Amount (wt.-%) |
| Neutralized acid alkyd (prepared as disclosed in EP 0 340 163 B1, p. 9, l. 45-51) | 11 |
| Acrylated oligomer (Ebecryl 600, of Cytec) | 7 |
| Surfactant (sodium dodecylbenzene-sulfonate) | 3 |

-continued

| Part I | |
|---|---|
| Component | Amount (wt.-%) |
| Mineral solvent (PKWF 6/9 neu, of Haltermann) | 4 |
| Talcum | 2 |
| Polyethylene wax (Ceridust 9615A, of Clariant) | 2 |
| Fusible wax (Carnauba wax) | 5 |
| Mineral filler (Sturcal L, of Specialty Minerals) | 24.5 |
| Total | 58.5 |

A second part of the ink was prepared by combining the following components, and grinding them on a three-roll mill, so as to form of a homogenous dispersion:

| Part II | |
|---|---|
| Component | Amount (wt.-%) |
| Modified alkyd (Urotuföl SB650 MO 60, of Reichhold Chemie, or the alkyd resin of part I) | 12.5 |
| Phenolic modified rosin based varnish (solution of Sylvaprint MP6364 of Arizona (45%) in PKWF 4/7 (15%) and linseed oil (40%)) | 5.5 |
| Mineral solvent (PKWF 6/9 neu, of Haltermann) | 1 |
| PB 15:3 blue pigment (Irgalite blue GLO, of CIBA) | 7 |
| Mineral filler (Sturcal L, of Specialty Minerals) | 9.5 |
| Total | 35.5 |

The final ink was prepared by combining on a three-roll mill the above parts I and II with the following additional components:

| Final ink | |
|---|---|
| Component | Amount (wt.-%) |
| Part I | 58.5 |
| Part II | 35.5 |
| Photoinitiator (Irgacure 819, of Ciba) | 2 |
| UV stabilizer (Florstab 1, of Floridienne) | 1.5 |
| Metal drier (blend of octa-soligen cobalt (12 parts) and Octa-soligen manganese (8 parts), of Borchers) | 2.5 |
| Total | 100 |

The viscosity of the final ink was adjusted with mineral solvent and additives, e.g. Aerosil, to about 1 to 40 Pa·s, preferably about 3 to 25 Pa·s, more preferably to about 6 to 15 Pa·s, measured on a cone-plate geometry at 1000 s$^{-1}$ and 40° C.

COMPARATIVE EXAMPLE 1

Modified 30 without Wax

The ink was prepared as described above in example 1, except that in part I no fusible wax was added. Instead, the amount of the mineral filler (Sturcal L, of Specialty Minerals) was raised to 29.5 wt.-% (based on the final ink composition) in order to compensate for the lack of fusible wax.

COMPARATIVE EXAMPLE 2

Standard

The ink was prepared as descried in example 1, except that no UV-curable resin was present.

A first part of the ink was prepared by combining the following components, and grinding them on a three-roll mill, so as to form a homogenous dispersion (the amounts are given as wt.-% with respect to the final ink composition):

| Part I | |
|---|---|
| Component | Amount (wt.-%) |
| Neutralized acid alkyd (prepared as disclosed in EP 0 340 163 B1, p. 9, l. 45-51) | 18 |
| Acrylated oligomer (Ebecryl 600, of Cytec) | — |
| Surfactant (sodium dodecylbenzene-sulfonate) | 3 |
| Mineral solvent (PKWF 6/9 neu, of Haltermann) | 4 |
| Talcum | 2 |
| Polyethylene wax (Ceridust 9615A, of Clariant) | 2 |
| Fusible wax (Carnauba wax) | 5 |
| Mineral filler (Sturcal L, of Specialty Minerals) | 24.5 |
| Total | 58.5 |

A second part of the ink was prepared by combining the following components, and grinding them on a three-roll mill, so as to form a homogenous dispersion (the amount of the alkyd resin and the filler in part II was increased to compensate for the lack of UV-photoinitiator and UV-stabilizer in the final ink):

| Part II | |
|---|---|
| Component | Amount (wt.-%) |
| Modified alkyd (Urotuföl SB650 MO 60, of Reichhold Chemie, or the alkyd resin of part I) | 14 |
| Phenolic modified rosin based varnish (solution of Sylvaprint MP6364 of Arizona (45%) in PKWF 4/7 (15%) and linseed oil (40%)) | 5.5 |
| Mineral solvent (PKWF 6/9 neu, of Haltermann) | 1 |
| PB 15:3 blue pigment (Irgalite blue GLO, of CIBA) | 7 |
| Mineral filler (Sturcal L, of Specialty Minerals) | 11.5 |
| Total | 39 |

The final ink was prepared by combining on a three-roll mill the above parts I and II with the following additional components:

| Final ink | |
|---|---|
| Component | Amount (wt.-%) |
| Part I | 58.5 |
| Part II | 39 |
| Photoinitiator (Irgacure 819, of Ciba) | — |
| UV stabilizer (Florstab 1, of Floridienne) | — |
| Metal drier (blend of octa-soligen cobalt (12 parts) and Octa-soligen manganese (8 parts), of Borchers) | 2.5 |
| Total | 100 |

The viscosity of the final ink was adjusted with mineral solvent and additives, e.g. Aerosil, to about 1 to 40 Pa·s, preferably about 3 to 25 Pa·s, more preferably to about 6 to 15 Pa·s, measured on a cone-plate geometry at 1000 $s^{-1}$ and 40° C.

COMPARATIVE EXAMPLE 3

Standard without Wax

The ink was prepared as described above in comparative example 2, except that in part I no fusible wax was added. Instead, the amount of the Mineral filler (Sturcal L, of Specialty Minerals) was raised to 29.5 wt.-% (based on the final ink composition) in order to compensate for the lack of fusible wax.

Measurements

The set-off resistance values were determined as follows: 10 intaglio prints were made on banknote paper (175×145 mm) on a trial press with the exemplary inks, using a standard, heated intaglio plate having fine, medium and deep engravings (up to 120 μm). The 10 printed sheets were immediately stacked on top of each other, with 10 blank interleaving sheets between them, and weight of 2 kg was placed on the stack. After 24 hours, the stack was separated, and the set-off to the interleaving sheets was evaluated on a statistical basis, by comparing each interleaving sheet with a scale of reference set-off sheets. A value between 1 (bad) and 6 (excellent) was attributed to each sheet, and the mean value of the 10 sheets was taken as being representative of the set-off of the ink in question.

The reference set-off sheets represent a standard intaglio image (FIG. 3) in a linear series of photometric graduations, going from perfect copy (set-off value 1) to no copy at all (set-off value 6). Set-off values for practicable inks must be close to 6.

The complex dynamic modulus G* (in Pa) of the inks in question was determined on a AR1000 rheometer from TA Instruments in oscillating mode at 25° C.; cone 4 degree, 2 cm diameter, frequency 1 Hz.

In FIG. 1, a plot of the experimentally determined complex dynamic modulus G* (in Pa) against the set-off resistance values (as determined above) is shown. FIG. 1 refers to intaglio inks which are formulated as given in Comparative Example 2 ("Standard") and in Comparative Example 3 ("Standard without wax"), with variations as to the type and the quantity of fusible wax, as well as solvent content. These inks do not contain any UV-curable components. The four inks to the left correspond to comparative example 3 (i.e. inks without wax). The four inks to the right of the graph correspond to Comparative Example 2 and contain different kinds and concentrations of fusible waxes. A first set of complex dynamic modulus values was determined on the freshly prepared inks (otherwise as described above) (triangular points in FIG. 1). A second set of set-off resistance values and of complex dynamic modulus values was measured on the same inks after a thermal cycle, in which the ink's temperature was raised to 80° C. (i.e. the temperature of the printing plate) and cooled to 25° C. again (square points in FIG. 1). Only the square points represent a (dynamic modulus/set-off) value pair; the triangular points, corresponding to the not thermally cycled inks, do only represent the dynamic modulus values of the corresponding inks before printing and have been extrapolated from the square points with respect to the set/off resistance values. For determining set-off values, the inks must noteworthy be printed, and therefore mandatory pass through a thermal cycling.

A glance at FIG. 1 shows that the inks without fusible wax (points to the left) show only a slight increase in G* after thermal cycling. These inks remain tacky after printing, and correspondingly produce set-off, as indicated by their lower set-off resistance values. The inks with fusible wax (points to the right) show a large increase in G* after thermal cycling. These inks lose their tackiness upon printing, and correspondingly avoid set-off, as indicated by their higher set-off resistance values.

The observed increase in complex dynamic modulus after the heating/cooling cycle is an indicator of the ink's internal structural change upon printing. It can be seen that inks showing a large increase of the complex dynamic modulus G* (i.e. the group of inks to the right of the graph, which comprise fusible wax) upon thermal cycling have higher set-off resistance values than inks showing a small increase of the complex dynamic modulus (i.e. the group of inks to the left of the graph, without fusible wax).

FIG. 2 illustrates the synergistic effect of the combination of fusible wax and UV-curable acrylate in an intaglio ink in preventing set-off after printing. The inks according to example 1 and comparative example 1 to 3 were applied as follows: A 15 micrometer thick layer of the ink in question was applied onto a 80° C. preheated glass plate using a SHINN applicator. The glass plate was placed at 80° C. in an oven for additional 10 seconds, then cooled to 25° C. again. Where indicated, the glass plate was then subjected to UV-irradiation (1 pass, 50 m/min, 150 W/cm, 2 UV lamps); this treatment is designated as "2×100 UV". The ink layer was subsequently scratched off the glass plate with a spatula and measured on the AR1000 rheometer.

Figure 2A:
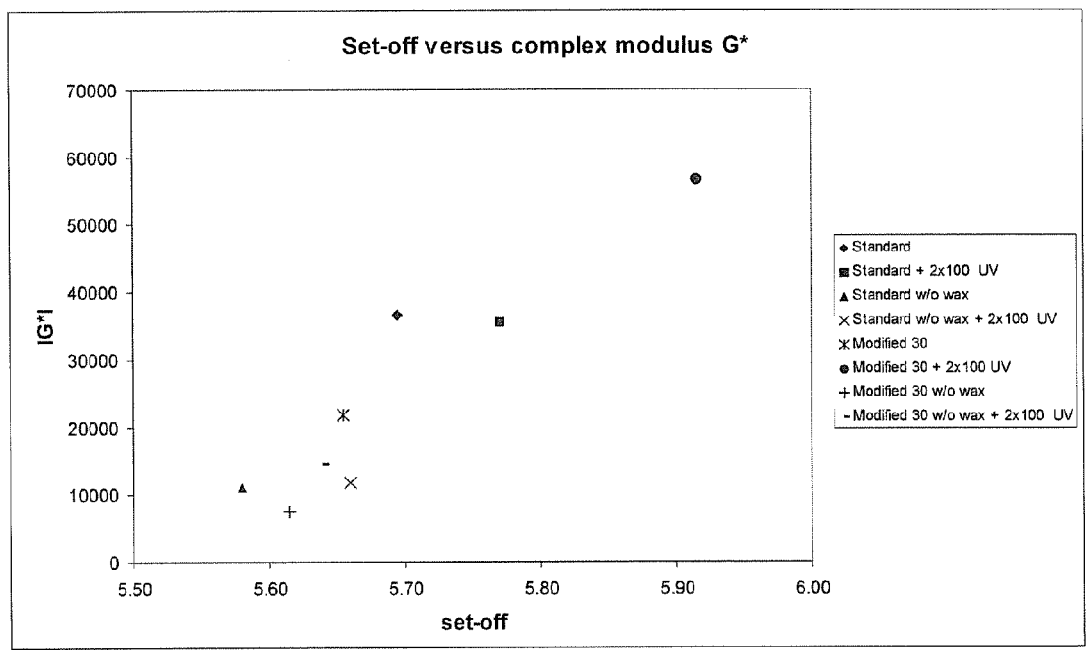
FIG. 2a shows a plot of the experimentally determined set-off value versus the complex dynamic modulus G*=G'+iG" [Pa, as an absolute value]

FIG. 2a shows a plot of the experimentally determined set-off resistance values (determined as described above) versus the complex dynamic modulus G* (in Pa as an absolute value).

Figure 2B:
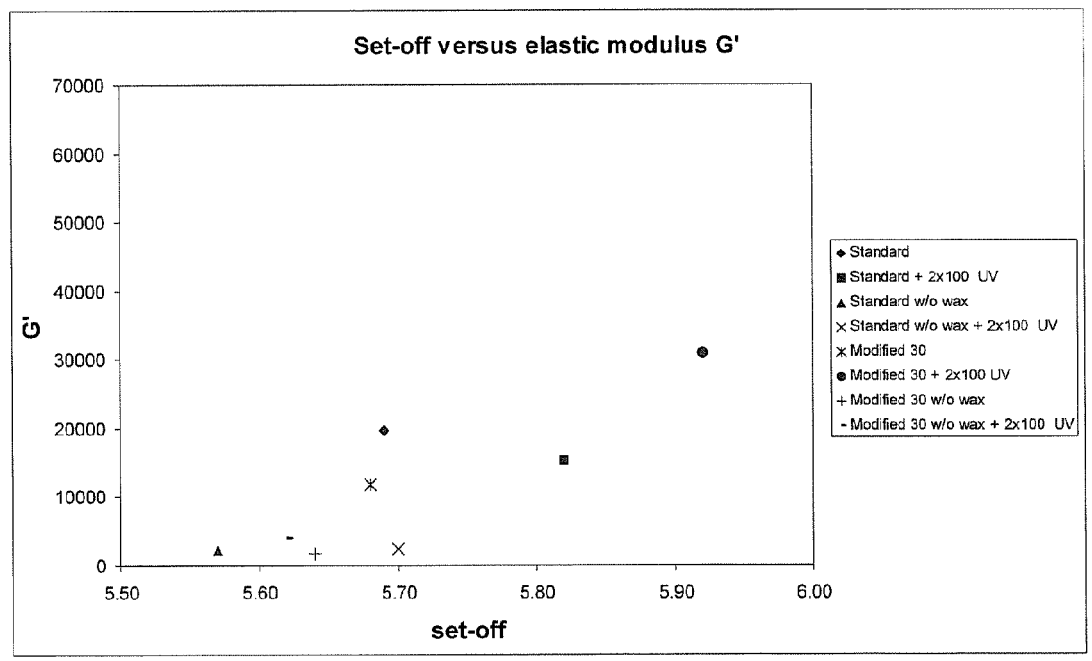
FIG. 2b shows a plot of the set-off value versus the elastic component G' (real part of G*; also called the storage modulus)

FIG. 2b shows a plot of the set-off value versus the elastic component G' (real part of G*; also called the storage modulus) of the measured complex dynamic modulus G*.

Figure 2C:
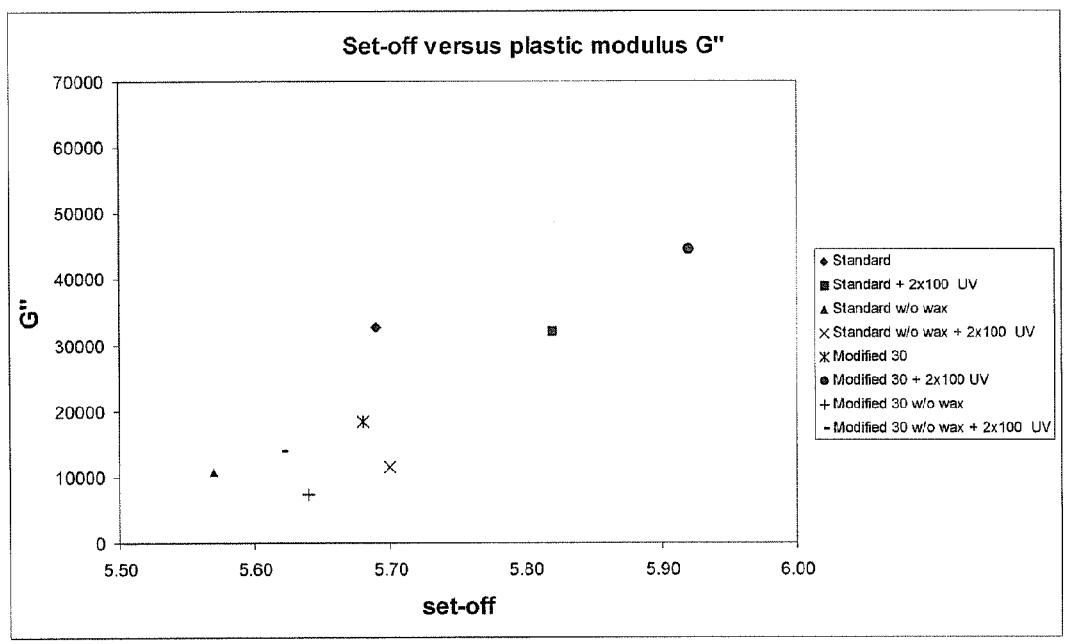
FIG. 2c shows a plot of the set-off value versus the plastic or viscous component G" (imaginary part of G*, also called the loss modulus).

FIG. 2c shows a plot of the set-off value versus the plastic or viscous component G" (imaginary part of G*, also called the loss modulus) of the measured complex dynamic modulus G*.

The ink of example 1, comprising both wax and UV-curable acrylate, and subjected to the above thermal cycle, followed by UV-irradiation ("Modified 30+2×100 UV"), has the highest value of complex dynamic modulus G* (Pa), and also provides the best set-off resistance values of all investigated inks. The set-off properties furthermore correlate in the same way with both components of the complex dynamic modulus, i.e. with the elastic (G') and with the plastic (G") modulus; the latter being the more important contributor to the complex dynamic modulus. In particular, an unexpectedly high increase of the set-off resistance value after the above thermal cycle was observed with the ink of example 1. Said increase exceeded the respective increase of the set-off resistance value of the other examined inks by far.

As can be inferred from FIG. 2a, the UV-irradiation of the ink of the present invention led to a more than twofold increase of the complex dynamic modulus G*. Even for the same ink without wax, an about twofold increase of the complex dynamic modulus G* was observed. On the other hand, for the standard ink, with or without wax, UV-irradiation did not show any noticeable effect on the complex dynamic modulus G*.

Figure 3:
FIG. 3 shows the intaglio-printed test image used to assess the set-off and drying properties of the inks (shown in FIG. 4a-d).

The cooperative effect of wax and UV-curable acrylate in preventing set-off was assessed as follows: FIG. 3 shows the intaglio-printed test image used to assess said set-off and drying properties of the inks. This test intaglio plate has different engraving depths, varying from shallow (fine-line pattern in the face and hair part), to middle-deep (hat part), to deep engraving (SICPA guilloches). The deep engraving yields the most sensitive parts on the printed image for assessing the set-off properties. The latter are assessed by subjecting a fresh print covered by a sheet of paper to a weight of 2 kg during 24 hours, then separating the sheet of paper from the print. The set-off image is the reverse of the printed image.

FIG. 4a-d illustrate the cooperative effect of a UV component and a fusible wax onto the set-off properties of the ink. The ink of example 1 was used in the cases shown in FIGS. 4b and 4d, whereas in the cases of FIG. 4a and FIG. 4c. the ink of comparative example 1 (i.e. the fusible wax (Carnauba wax) was replaced by 5% mineral filler) was used. In the cases shown in FIGS. 4c and 4d, a UV-irradiation as described above was carried out, whereas in the cases shown in FIGS. 4a and 4b, no UV-irradiation was carried out.

Figure 4A:
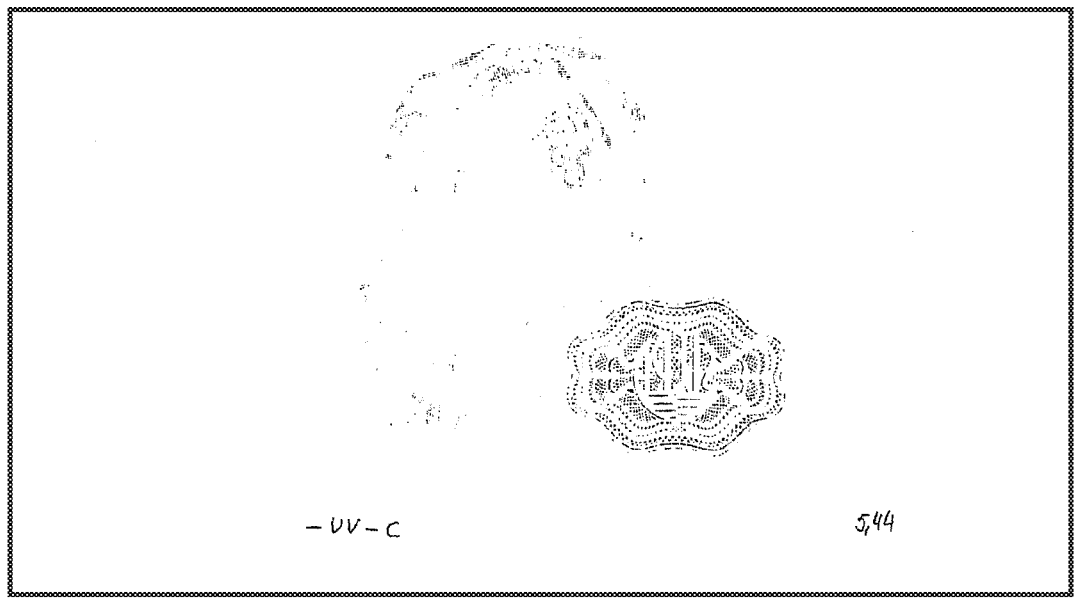
Figure 4B:
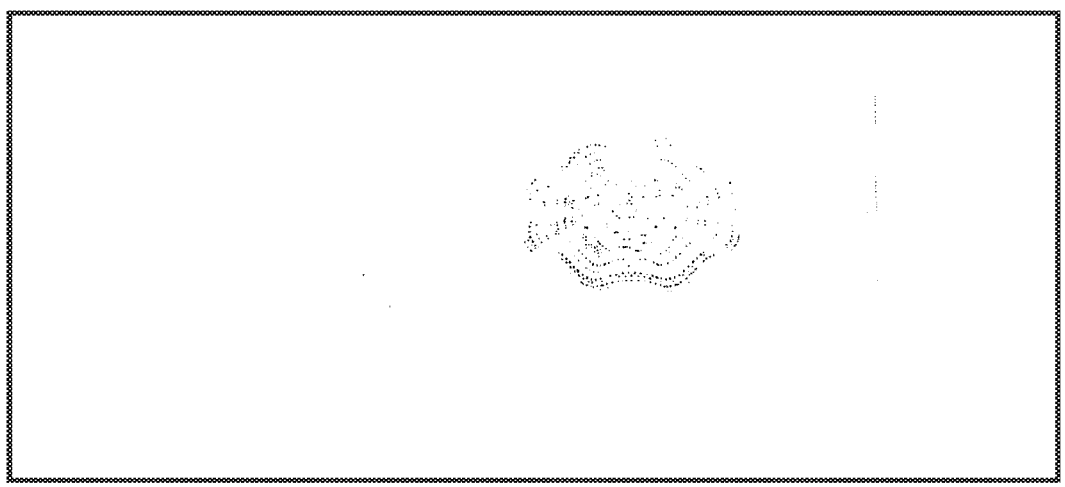
Figure 4C:
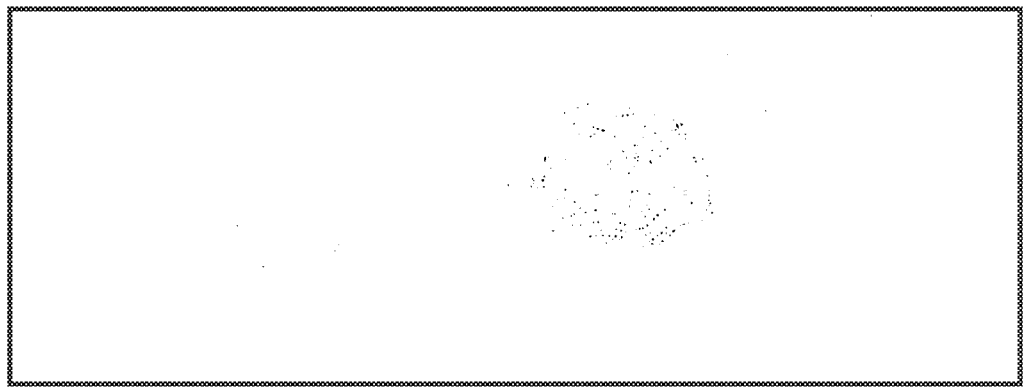
Figure 4D:
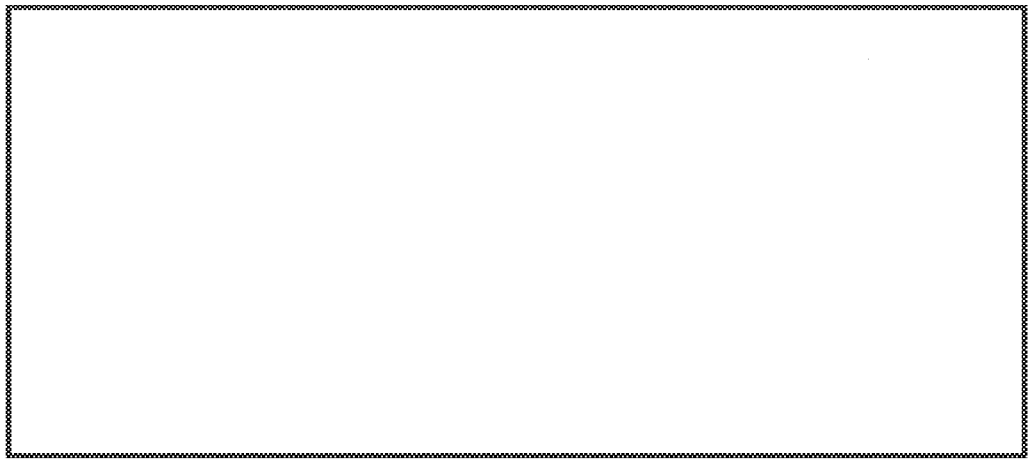

In the absence of UV-irradiation and wax (FIG. 4a, comparative example 1), a bad set-off note (5.44) resulted. The presence of fusible wax (FIG. 4b, example 1) already considerably improved the set-off note (5.60). UV-irradiation in the absence of fusible wax (FIG. 4c, comparative example 1) gave a similar result (5.66). Set-off was completely absent (FIG. 4d, example 1) in the presence of fusible wax after UV-irradiation (note 5.90).

The invention claimed is:

1. An intaglio printing ink composition comprising at least one oxidatively curable principal material in an amount of 25 to 40 wt-% of the total printing ink, at least one UV-curable material in an amount between 2 and 15 wt-% of the total printing ink, at least one fusible wax in an amount greater than 0 and up to 10 wt-% of the total printing ink, at least one oxypolymerization drier, and at least one photoinitiator,
wherein the dynamic modulus (G*) of the composition increases at least 50% after thermal cycling from 25° C. to 80° C. to 25° C. and irradiation with a curing dose of UV light.

2. Intaglio printing ink composition according to claim 1, wherein said at least one fusible wax is present in an amount between 2 and 5 wt-% of the total printing ink.

3. Intaglio printing ink composition according to claim 1, wherein said ink further comprises pigments, fillers, additives and solvents.

4. Intaglio printing ink composition according to claim 1, having a viscosity in the range of about 1 to 40 Pa·s, measured on a cone-plate geometry at $1000 \text{ s}^{-1}$ and 40° C.

5. Intaglio printing ink composition according to claim 1, wherein said oxidatively curable material is selected from the group consisting of the alkyd resins and the modified alkyd resins of synthetic or natural origin, neutralized acid alkyds, and drying vegetable oils.

6. Intaglio printing ink composition according to claim 5, wherein said modified alkyd resins of synthetic or natural origin are phenol-, epoxy-, urethane-, silicone-, acryl- and vinyl-modified alkyd resins.

7. Intaglio printing ink composition according to claim 1, wherein said UV-curable material is an acrylate comprised in an amount of 4 to 8% by weight of the total printing ink.

8. Intaglio printing ink composition according to claim 7, wherein said acrylate is selected from the group consisting of the amino acrylates, the epoxy acrylates, the polyester acrylates, the urethane acrylates, the self-photoinitiating oligomeric acrylates, the dendrimeric acrylates, and mixtures thereof.

9. Intaglio printing ink composition according to claim 1, wherein the melting point or melting range of said fusible wax is between 50 to 120° C.

10. Intaglio printing ink composition according to claim 1, wherein said fusible wax is selected from the group consisting of refined Montan wax, Montanic-acid, -amide, -ester; modified or saponified Montan wax, Carnauba wax, long chain ester wax, and mixtures thereof.

11. Intaglio printing ink composition according to claim 1, wherein said oxypolymerization drier is based on transition metal salts and other chemical elements which are soluble in the printing ink.

12. Intaglio printing ink composition according to claim 11, wherein said oxypolymerization drier is a combination of cobalt and manganese carboxylates or a combination of cobalt, manganese and zirconium carboxylates, wherein the carboxylate is a long-chain carboxylic acid anion.

13. Intaglio printing ink composition according to claim 11, wherein said oxypolymerization drier is a combination of cobalt octoate, manganese octoate and zircon octoate in a hydrocarbon solvent.

14. Intaglio printing ink composition according to claim 1, wherein said oxypolymerization drier is present in amounts of up to 5 wt-% of the total printing ink.

15. Intaglio printing ink composition according to claim 1, wherein said photoinitiator is selected from the group consisting of the α-aminoketones, the α-hydroxyketones, the phosphine oxides, the thioxanthones, the oligomeric thioxanthones, the oligomeric amino benzoates, and the oligomeric benzophenones.

16. Intaglio printing ink composition according to claim 1, wherein said photoinitiator is comprised in the ink in an amount of up to 5% by weight of the printing ink.

17. Intaglio printing ink composition according to claim 1, further comprising a photoinitiator-stabilizer.

18. Intaglio printing ink composition according to claim 17, wherein said photoinitiator-stabilizer is comprised in the ink in an amount of up to 3% by weight of the total printing ink.

19. Process for producing an intaglio printing ink composition comprising:
a) grinding together at least one oxypolymerization-curable material, at least one UV-curable material, and at least one fusible wax, to obtain a homogeneous dispersion;
b) grinding together at least one oxypolymerization-curable material, and at least one pigment, to obtain a homogeneous dispersion; and
c) mixing and grinding together the dispersion of a), the dispersion of b), an oxidative drier, and a photoinitiator, wherein said oxypolymerization-curable material is present in an amount of 25 to 40 wt-% of the total printing ink, said UV-curable material is present in an amount between 2 and 15 wt-% of the total printing ink, and said fusible wax is present in an amount greater than 0 and up to 10 wt-% of the total printing ink, and wherein the dynamic modulus (G*) of the composition increases at least 50% after thermal cycling from 25° C. to 80° C. to 25° C. and irradiation with a curing dose of UV light.

20. Process according to claim 19, wherein said grinding is made on a three-roll mill.

21. Process according to claim 19, wherein said oxypolymerization-curable material is an alkyd resin.

22. Process according to claim 19, wherein said UV-curable material is an acrylate.

23. Process according to claim 19, wherein in a) or b) additionally fillers and solvents are incorporated.

24. Process according to claim 19, wherein in c) additionally a photoinitiator stabilizer is incorporated.

25. Process according to claim 19, wherein a first oxypolymerization-curable material is used in a) and a second, different oxypolymerization-curable material is used in b), to assure compatibility with the UV-curable acrylate and with the pigment, respectively.

26. Process according to claim 25, wherein said first oxypolymerization-curable material is an alkyd resin.

27. Process according to claim 25, wherein said second oxypolymerization-curable material is an alkyd resin.

28. Method of intaglio printing using an intaglio printing ink according to claim 20, comprising:
   a) intaglio-printing the ink onto a substrate, including cycling the ink's temperature from room temperature to printing plate temperature and back to room temperature;
   b) subjecting the printed document to UV-radiation subsequently after the printing operation; and
   c) storing the printed document for more than a day to allow for oxidative curing.

29. Security document or document of value, comprising an imprint made with an intaglio printing ink composition according to claim 1.

30. Security document or document of value according to claim 29, wherein said security document or document of value is a passport, an identification document, a diving license, a banknote, a stock certificate, a tax banderole, an excise stamp, or a security label.

* * * * *